United States Patent
Letzel et al.

(10) Patent No.: US 8,337,908 B2
(45) Date of Patent: Dec. 25, 2012

(54) PLANT EXTRACT FROM LOW-THC CANNABIS FOR THE TREATMENT OF DISEASE

(76) Inventors: Heinz Letzel, Grainau (DE); Thomas Ebell, legal representative, Murnau (DE); Regina Klaeger, Landsberg (DE); Rudolph Klaeger, Landsberg (DE)

( * ) Notice: Subject to any disclaimer, the term of this patent is extended or adjusted under 35 U.S.C. 154(b) by 0 days.

(21) Appl. No.: 12/679,987

(22) PCT Filed: Sep. 26, 2008

(86) PCT No.: PCT/DE2008/001581
§ 371 (c)(1),
(2), (4) Date: Mar. 25, 2010

(87) PCT Pub. No.: WO2009/039843
PCT Pub. Date: Apr. 2, 2009

(65) Prior Publication Data
US 2010/0216872 A1 Aug. 26, 2010

(30) Foreign Application Priority Data
Sep. 26, 2007 (DE) .......................... 10 2007 046 086

(51) Int. Cl.
*A01N 65/00* (2009.01)
(52) U.S. Cl. ....................................................... 424/725
(58) Field of Classification Search ........................ None
See application file for complete search history.

(56) References Cited

U.S. PATENT DOCUMENTS
6,403,126 B1 6/2002 Webster et al.

2004/0049059 A1 3/2004 Mueller
2004/0138293 A1 7/2004 Werner et al.
2007/0032544 A1* 2/2007 Korthout et al. .............. 514/454

FOREIGN PATENT DOCUMENTS
| DE | 19833567 C1 | | 8/1999 |
| WO | 0232420 A | | 4/2002 |
| WO | 02069993 A | | 9/2002 |
| WO | 2005072719 A | | 8/2005 |
| WO | WO 2005/072719 | * | 8/2005 |

OTHER PUBLICATIONS

Vogl et al., Journal of Industrial Hemp, vol. 9(1), 2004, pp. 51-68.*
Fairbairn et al., Br. J. Pharmac., 1981, 72, 401-409.*
*Cannabis* spp., 9 pages, 2010.*
Vogl C.R. et al.: "Hemp (*Cannabis sativa* L) as a Resource for Green Cosmetics: Yield of Seed and Fatty Acid Compositions of 20 Varieties Under the Growing Conditions of Organic Farming in Austria" Journal of Industrial Hemp, vol. 9, No. 1, 2004, pp. 51-68, XP002536675 p. 53, line 3-line 9, p. 56, line 5-line 26 p. 66, paragraph 2.
Fiocchi A et al: "The efficacy and safety of gamma-linolenic acid in the treatment of infantile atopic dermatitis" Journal of International Medical Research, vol. 22, No. 1, 1994, pp. 24-32, XP008108315 ISSN: 0300-0605 the whole document.

* cited by examiner

*Primary Examiner* — Michael Meller
(74) *Attorney, Agent, or Firm* — Connolly Bove Lodge & Hutz LLP

(57) ABSTRACT

The present invention relates to a plant extract from a low-tetrahydrocannabinol (THC) variety of *Cannabis sativa* subsp. *sativa* for the treatment of disease. The invention further relates to the production of the extract and pharmaceutical compositions comprising said extract and the uses thereof.

1 Claim, No Drawings

PLANT EXTRACT FROM LOW-THC CANNABIS FOR THE TREATMENT OF DISEASE

The present invention relates to a plant extract from a low-tetrahydrocannabinol (THC) variety of *Cannabis sativa* subspecies *sativa* for the treatment of disease. Furthermore, the invention relates to the production of the extract and pharmaceutical or topical compositions, which contain this extract, and the uses thereof.

The plant species *cannabis* belongs to the family of the hemp plants and according to more recent findings comprises a single species (*Cannabis sativa*), which occurs in 3 subspecies: industrial hemp (*Cannabis sativa* subspecies *sativa*) L., Indian hemp (*Cannabis sativa* subspecies *indica*) Lam., and ruderal hemp (*Cannabis sativa* variety *spontanea*). Depending on the intended use, a differentiation is made between intoxicant or medicinal hemp, having the drug THC, and industrial and decorative hemp.

*Cannabis* is popular as a renewable raw material because of its ready cultivation and complete usability. No herbicides are required, because the plants already shadow the soil completely after a few days, so that weeds no longer have light. In addition, *cannabis* is extraordinarily pest-resistant and low-maintenance. *Cannabis* produces more biomass than any other native useful plant, is usable in a great manifold of ways in the economy, and is prized because of its high durability, environmental compatibility, and low energy balance.

Manifold different products from all fields of daily life may be produced from *cannabis*, such as materials (construction slabs, insulation materials, sealants, etc.), cosmetics (creams, massage oil, soap, etc.), foods (animal feed, oil, margarine, fats, etc.), oils, oil products (oil for the production of printing inks and/or oil paints and putty and spackling compounds, plastics made of oil, surfactants), papers, nonwoven materials, pulps, natural insulation materials and fabrics (short and long fiber).

The so-called cannabinoids are found as components in *cannabis* plants. It is estimated that the resin of the *cannabis* plant contains over 70 different cannabinoids, some of which, such as THC, have psychotropic effects. The target structures of the cannabinoids upon consumption in the human organism are the cannabinoid receptors CB-1 and CB-2 of the endocannabinoid system. The physiological ligand of these receptors is the arachidonic acid derivative anandamide. Currently, the cannabinoid THC is known as a medical drug above all. Thus, for example, semisynthetic THC, dronabinol, is usable in Germany and other countries as a prescription narcotic (trade name Marinol®) for anorexia and cachexia in HIV and AIDS patients, and as an antiemetic for nausea and vomiting under cytostatic or radiation therapy in the context of a cancer therapy. The completely synthetic THC derivative nabilon has a similar indication. In addition, THC is in the clinical testing phase for the treatment of glaucoma and autoimmune diseases, such as multiple sclerosis, Crohn's disease, or ulcerative colitis. A further known, but non-psychoactive cannabinoid from female hemp plants of *Cannabis sativa* is cannabidiol (CBD). Medicinally, it relieves cramps and anxiety, is anti-inflammatory, is an antinauseant, and reduces internal eye pressure.

WO 2005/072719 describes a plant extract, which contains at least one acid cannabinoid and also has a low THC content of 0-5 wt.-%. This plant extract is preferably obtained from the flowers of the varieties *Cannabis sativa* subspecies *sativa* and *Cannabis sativa* subspecies *indica* using liquid extraction methods, preferably under non-decarboxylating conditions. The non-decarboxylating conditions are necessary to keep the THC content as low as possible. In addition, the use of the plant extracts for the production of a medication for the treatment of inflammatory skin diseases, such as dermatitis or psoriasis, is noted, but without any experimental data which could confirm the effectiveness.

In addition, a pharmaceutical composition is disclosed in US 2007/0060639, which comprises at least one tricyclic cannabinoid for intranasal administration. Furthermore, the use of this pharmaceutical composition in the event of allergic rhinitis is described.

An example of a method for producing a *cannabis* extract is disclosed in US 2003/0017216 A1. For this purpose, the plant material is admixed with a solvent, such as isopropanol, for a specific period of time. The period of time is less than that which would be necessary to obtain an equilibrium concentration of dissolved cannabinoids in the solvent. The solvent and the dissolved cannabinoids are subsequently separated from the plant material.

The medicinal effectiveness of a plant extract from the low-THC variety *Cannabis sativa* subspecies *sativa* has been completely neglected and unstudied up to this point. A plant extract of this type not only has the advantage of cost-effective production; through the legal cultivation of low-THC varieties, such as Futura 75, a possible conflict in regard to the narcotic code is also entirely avoided above all.

Diseases of the allergically and immunologically related spectrum disorder are currently predominantly treated using cortisone preparations (also known as glucocorticoid preparations), or calcineurin inhibitors (from the class of cytostatics), which are subject to side effects. However, the topically treatable extent of the skin surface is limited both with the cortisone preparations and also with the calcineurin inhibitors in that upon large-area application, systemically-relevant resorption over the treated skin area must be expected. The side effects of both therapy principles thus come to bear in a clinically relevant manner in the entire body.

In addition to the restriction of the extent of the treatable skin area, the therapy duration is also limited. However, many disease symptoms which require cortisone or are only treatable by calcineurin inhibitors, such as neurodermitis, are chronic diseases, which thus require continuous treatment, having a significant level of suffering of the affected patients. The treatment using calcineurin inhibitors is limited to at most four weeks per cycle. This is similarly true for the treatment using cortisone preparations. In both cases, after the cessation of the therapy, which is medically required to avoid grave and sometimes irreversible side effects, an acute exacerbation of his symptoms ("rebound effect") which is extremely stressful for the patient, must be expected by the patient.

There is no rigid scheme for the treatment using cortisone in regard to the local side effects. A significant atrophy of the treated skin area must nonetheless fundamentally be expected. In addition to cosmetic skin changes ("leather skin"), which restrict the quality of life, and which have significant relevance above all upon disease affliction in the facial area, functionally relevant skin changes have also been observed. The skin atrophy is accompanied above all with a vulnerability of the paper-thin skin areas, which is increased upon illness.

Although both the cortisone preparations and also the calcineurin inhibitors display good effectiveness in the great majority of patients, the compliance is relatively low because of the above-mentioned and thus feared side effects. The patients frequently accept the symptoms of the illness because of fear of the side effects of the listed substance groups.

It is thus the object of the present invention to provide an effective medication, which is free of side effects, for the treatment of diseases, preferably for the treatment of diseases of the allergically and immunologically related spectrum disorder, based on plants, which is not only cost-effective and simple to produce, but rather also achieves very high compliance with the patients because of its rapid and convincing initial effect and lack of side effects (up to this point). The object of the present invention is achieved in a first aspect by a plant extract made of the flowers and flower-proximal leaves and/or stems and/or roots and/or seeds, preferably the flowers and flower-proximal leaves of a low-tetrahydrocannabinol (THC) variety of Cannabis sativa subspecies sativa for the treatment of diseases ("plant extract" hereafter).

In the scope of this invention, a "low-tetrahydrocannabinol (THC) variety" is understood as a variety which, in such a plant extract, has less than 5%, preferably less than 2%, in particular less than 0.5 to 0.2% or down to 0.1 or 0% (wt.-%) THC content. In particular, these quantities of THC are to be understood as not representing a clinically relevant concentration.

Surprisingly, it has been shown by the experiments performed in the scope of the invention that this plant extract has an effectiveness comparable or even superior to cortisone and calcineurin (without their side effects!) in regard to diseases of the allergically and immunologically related spectrum disorder. In patients having neurodermitis, which has a highly dramatic clinical course, the need, which is in the foreground for almost all patients, for itching relief could be dramatically improved in particular in comparison to the previously ordered cortisone or calcineurin inhibitors. The clinical relevance results from the secondary results of this cardinal guiding symptom for neurodermitis: scratching until bloody at the affected skin areas because of the unrelieved itch, with consequent lichenification. In contrast to the symptom influence (itching), which only begins within days after cortisone therapy, the guiding symptom of itching can be improved within a few minutes using the low-THC plant extract in a pharmaceutically suitable administration form. Through this improvement of the clinical symptom "itching", which is in the foreground, secondary symptoms such as scratch-related skin lesions with bleeding, followed by subsequent lichenification, are clinically visibly improved within a few days. This is of very high significance above all for women and/or in the facial area.

In addition, this plant extract has not displayed any side effects up to this point. Therefore, all of the above-mentioned side effects under the treatment using cortisone or calcineurin inhibitors are not a concern and/or may even be healed, in particular in regard to the topical side effects of longer cortisone therapy. The use of cortisone and calcineurin can be completely avoided. For patients who, for the cited substance classes, are either therapy resistant or were already suffering from their side effects or who have rejected the therapy using the substance groups, this represents a completely novel therapy approach.

Furthermore, a clinically distinct antimycotic effect, which was also not suspected up to this point, was shown, which could prove to be very valuable both topically and also systemically, above all because of its rapid initial effect, in the further therapy spectrum. This effectiveness relates to both saprophytes and also dermatophytes and yeast fungi. The relevance of this antimycotic effect results, beyond the effectiveness having little or no side effects, from both the necessity of applying antimycotic agents such as metronidazole (both topically and also systemically) for various skin diseases, and also its significant side effect potential.

According to the surprising effectiveness of the plant extract of the present invention described above, this extract is also used for the production of a pharmaceutical, preferably for the treatment of neurodermitis, contact eczema, allergies, the prevention or treatment of phototoxic reactions, the treatment of inflammatory, itching dermatoses, rosacea, perioral dermatitis, acne, acne conglobata, psoriasis (vulgaris, arthropathica, pustulosa), mosquito bites, skin atrophy (in particular also cortisone-related skin changes), allergic rhinitis, privinismus, conjunctivitis, otitis externa, bronchial asthma, Crohn's disease, ulcerative colitis, sarcoidosis, or inflammatory-rheumatic diseases of the soft tissue or joints, and mycoses. Inflammatory, itching dermatoses in the meaning of the present invention are understood in particular as diseases selected from the group comprising rosacea, perioral dermatitis, psoriasis vulgaris, psoriasis pustulosa, acne, acne conglobata.

Inflammatory-rheumatic diseases in the meaning of the present invention are understood as diseases selected from the group comprising chronic polyarthritis, Bechterew's disease, psoriasis arthritis, polymyalgia rheumatica, collagenoses, and vasculitides.

In the scope of this invention, the term "neuroderm(at)itis" (also, better: atopical dermatitis or "atopical eczema") is understood as an increasingly frequently occurring spasmodic skin disease, which occurs in particular in adolescents. The skin of a neurodermitis sufferer is highly sensitive in the acute phase and can react allergically to psychic and physical stressors and to an entire array of individually varying environmental factors and toxins. In the acute phase, the skin is inflamed and the affected individual particularly suffers from the agonizing itching. As far as is known, neurodermitis is not a result of a disease of the internal organs, but rather of inflammatory free-radical producing processes of the external skin layers, so that a positive influence can be taken here by external application in a topical application form using a dermatological or cosmetic composition, for example, in the form of salves, creams, or gels.

"Mycoses" in the meaning of the present invention are fungal diseases, which are typically triggered by thread fungi or sprout fungi. A differentiation is made for this purpose between superficial and systemic mycoses. Superficial mycoses may affect the entire body, foot fungus (Tinea pedis) is the most well known, but the mucosa may also be affected (thrush or candidiasis).

Furthermore, mycoses and neurodermitis may exist adjacent to one another, in particular in skin folds (behind the knee, etc.).

The plant extract of the present invention can be obtained by any extraction method known to one skilled in the art. For extracts which may also be used as directly applicable liquid pharmaceuticals, the following extraction agents are suitable: cold water, table salt solution, diluted acetic acid, sweet wine, ethanol-water mixtures, ethanol, other low-molecular-weight alcohols, acetone, esters, ethers, and mixtures thereof. Methanol, organic solvents such as acetone, ether, dichloromethane, and supercritical gases, vacuum extraction, and freeze-drying are typical and known to one skilled in the art for obtaining dry extracts. For this purpose, one may select between simple extraction methods selected from the group comprising resting maceration, moving maceration, digestion, percolation, re-percolation, evacolation and diacolation, and special extraction methods selected from the group comprising the combination of maceration and percolation, ultrasonic extraction, counter flow extraction, and extraction using separators, centrifuges, and decanters. These methods are known to one skilled in the art and reference is made, for example, to Hagers Handbuch der Pharmazeutischen Praxis [Hager's Handbook of Pharmaceutical Practice] (5th edition, volume 2; pages 1026-1030, Springer Verlag, Berlin-Heidelberg-New York (1991)). Fresh plants or plant parts may be used as the starting materials, however, one typically starts with dried plants and/or plant parts, which may be mechanically pulverized before the extraction. All pulverization methods known to one skilled in the art are suitable for this purpose, crushing using a mortar is cited as an example.

All solvents having a specific polarity, preferably organic solvents, water (distilled or non-distilled) or mixtures of organic solvents and water, in particular low-molecular-weight alcohols, esters, hydrocarbons, ketones, or halogenated hydrocarbons having greater or lesser water content may be used as the solvent for performing the extractions. Examples are protic (water, alcohols, acids, primary and secondary amines) and aprotic (acetonitrile, dimethyl formamide, dimethyl sulfoxide, hexamethyl phosphoric acid triamine, nitromethane, tert-amine) solvents. Extraction using water, methanol, ethanol, propanol, isopropanol, pentane, hexane, heptane, acetone, chloroform, propylene glycols, polyethylene glycols, ethyl acetate, dichloromethane, trichloromethane, and mixtures thereof is particularly preferred. The extraction is typically performed at 15 to 25° C. (aqueous extracts) or at 20 to 35° C. (low-molecular-weight alcohols), fundamentally preferably at room temperature, in order to reliably protect temperature-sensitive extract components. After the extraction, the obtained raw extracts may optionally be subjected to further typical steps, such as purification, concentration, and/or de-coloring. If desired, the extracts thus produced may be subjected to a selective separation of individual undesired components, for example. The extracts may subsequently also be subjected to a spray or freeze-drying, for example. The term "extract" according to the present invention is accordingly understood as a material and/or material mixture, which is obtained by one or more extraction and/or other method steps from the hemp plant.

In a particularly preferred embodiment, the plant extract of the present invention is obtained using an extraction medium, solvent, and/or mixture of solvents selected from the group comprising water, table salt solution, low-molecular-weight alcohols, acetone, esters, and ethers. 0.9% table salt solution, ethanol, or isopropanol is preferably used as the extraction medium, more preferably 90% ethanol or 70% isopropanol.

According to a preferred embodiment of the present invention, the low-THC *Cannabis sativa* subspecies *sativa* variety Futura 75 is used for obtaining the plant extract. A further aspect of the present invention relates to a method for producing a plant extract from the flowers and flower-proximal leaves of a low-THC *Cannabis sativa* subspecies *sativa*, comprising the steps of a) drying the flowers and/or flower-proximal leaves and/or stalks and/or roots and/or seeds, b) pulverizing the flowers and/or flower-proximal leaves and/or stalks and/or roots and/or seeds, and c) extracting the flowers and/or flower-proximal leaves and/or stalks and/or roots and/or seeds. The method is preferably performed using flowers and/or flower-proximal leaves, because the most drug is contained here.

According to a preferred embodiment, the extraction comprises the steps C-1) admixing the flowers and flower-proximal leaves for 24 hours-48 hours or 12 hours-48 hours with an extraction medium at room temperature and C-2) filtering the extract.

In still a further preferred embodiment, the method of the present invention comprises the step d) freeze-drying the acquired extract and/or vacuum extraction of the acquired extract. In a preferred embodiment, the method of the present invention uses solvents and/or mixtures of solvents selected from the group comprising water, table salt solution, low-molecular-weight alcohols, acetone, esters, and ethers, preferably 0.9% table salt solution, ethanol, or isopropanol, more preferably 90% ethanol or 70% isopropanol as the extraction medium.

In a particularly preferred embodiment, the low-THC *Cannabis sativa* subspecies *sativa* variety Futura 75 is used in the method of the present invention. However, it can also be replaced by any other *Cannabis sativa* variety having a THC content according to the current state of the national legal guidelines (in the German narcotics code currently 0.2%).

A further object of the present invention comprises a pharmaceutical composition, which comprises a plant extract, preferably made of the flowers and flower-proximal leaves of a low-THC *Cannabis sativa* variety, preferably the low-THC *Cannabis sativa* subspecies *sativa* variety Futura 75.

The invention also relates to a cosmetic or dermatological composition in a topical application form, which comprises a plant extract, preferably made of the flowers and flower-proximal leaves of a low-THC *Cannabis sativa* variety, preferably the low-THC *Cannabis sativa* subspecies *sativa* variety Futura 75.

In a special embodiment, the pharmaceutical or dermatological composition further comprises pharmaceutically suitable aids and additives. The pharmaceutical agents and/or compositions of the invention are produced using typical solid or liquid carriers or diluents and typical pharmaceutical and technical aids according to the desired type of application having a suitable dosage in a way known per se. Preferred preparations comprise an administration form which is suitable for topical, oral, inhaled, intranasal, enteral or parenteral, for example, i.p. (intraperitoneal), i.v. (intravenous), i.m. (intramuscular), or percutaneous application. Such administration forms are, for example, tablets, film tablets, dragées, pills, capsules, powders, creams, salves, lotions, liquids, such as syrups, gels, and injectable liquids, for example, for i.p., i.v., i.m., or percutaneous injection, nasal sprays or also inhalation sprays, etc. Furthermore, depot forms, such as implantable preparations, and suppositories are also suitable. The individual preparations release the extracts according to the invention to the body gradually or the entire quantity in a short time depending on their type. For oral administration, capsules, pills, tablets, dragées, and liquids or other known oral administration forms may be used as the pharmaceutical preparation. In this case, the pharmaceuticals may be formulated so that they release the drugs in a short time and discharge them to the body or have a depot effect, so that a longer-lasting, slow supply of drug to the body is achieved. The dosing units may contain one or more pharmaceutically compatible carriers in addition to at least one plant extract according to the invention, such as materials for setting the rheology of the pharmaceutical, surfactants, solution mediators, microcapsules, microparticles, granules, diluents, binders, such as starch, sugar, sorbitol, and gelatin, and also fillers such as silicic acid and talcum, lubricants, colorants, odorants, and other materials.

Corresponding tablets may be obtained, for example, by mixing the extract according to the invention with known aids, for example, inert diluents such as dextrose, sugar, sorbitol, mannitol, polyvinyl pyrrolidone, disintegrating agents such as cornstarch or alginate, binders such as starch or gelatin, lubricants such as carboxy polymethylene, carboxy methylcellulose, cellulose acetate phthalate, or polyvinyl acetate. The tablets may also comprise multiple layers.

Correspondingly, dragées may be produced by coating cores produced similarly to tablets using agents typically used in dragée coating, such as polyvinyl pyrrolidone or shellac, gum Arabic, talcum, titanium oxide, or sugar. The dragée shell can comprise multiple layers, the aids listed above for the tablets being able to be used.

Drugs may also be formulated in the form of a solution, which is intended for oral or topical administration and which contains, in addition to an active plant extract according to the invention, a pharmaceutically compatible oil and/or a pharmaceutically compatible lipophilic, surfactant substance, and/or a pharmaceutically compatible, hydrophilic surfactant substance, and/or a pharmaceutically compatible water-miscible solvent as components. Creams, salves, lotions, and tinctures may also be used for external application. These administration forms frequently contain aids, for example, materials for setting the rheology of the pharmaceutical, surfactants, preservatives, solution mediators, diluents, materials for increasing the permeation capability for the extracts according to the invention through the skin, colorants, odorants, and skin protection agents, such as conditioners and moisture regulators. Together with the extracts according to the invention, other drugs may also be contained in the pharmaceutical (Ulimanns Enzyklopädie der technischen Chemie [Encyclopedia of Technical Chemistry], volume 4 (1953), pages 1-39; J. Pharm. Sei. (1963) 52:918 et seq., H. V. Czetsch-Lindenwald, Pharm, hd. (1961) 2:72 ff, Fiedler, Lexikon der Hilfsstoffe für Pharmazie, Kosmetik and angrenzende Gebiete [Lexicon of Aids for Pharmacy, Cosmetics, and Related Fields], Cantor A G (1971)).

Corresponding cosmetic compositions of the plant extracts according to the invention may be provided similarly according to the typical formulations known for one skilled in the art in a topical application form.

In a further embodiment, the cosmetic or dermatological preparation according to the invention can therefore be produced for topical use ("topical composition") in the form of a salve, cream, gel, lotion (skin cream), paste, or preferably an emulsion. Water-free systems are also possible. Emulsions are generally understood as heterogenous systems which comprise two or more liquids which are not miscible or are only miscible with one another to a limited extent, which are typically designated as phases. In an emulsion, one of the two liquids is dispersed in the other liquid in the form of ultrafine droplets. If the two liquids are water and oil, and oil droplets are finely distributed in the water, it is an oil-in-water emulsion (O/W emulsion). The fundamental character of a O/W emulsion is given by the water. In a water-in-oil emulsion (W/O emulsion), the reverse principle applies, in that the fundamental character is determined here by the oil. Furthermore, mixed systems such as water-in-oil-in-water emulsions (W/O/W emulsion) and oil-in-water-in-oil emulsions (O/W/O emulsions) are known. All cited emulsions are suitable according to the invention.

The water-free systems suitable according to the invention include pure oil preparations such as skin oils. Pastes which are also usable containing the preparation according to the invention are distinguished in that they comprise the same or similar components as an emulsion but are essentially water-free. The terms oil phase and lipid phase are used synonymously in the scope of the present invention. In a further preferred embodiment, the preparation according to the invention can contain an emulsifier as a further component. In a very preferred embodiment, this emulsifier can be an O/W emulsifier.

Emulsifiers may advantageously be selected from the group of non-ionic, anionic, cationic, or amphoteric emulsifiers.

The plant extracts according to the invention may also be applied in suitable solutions, such as a physiological table salt solution, as an infusion or injection solution, nasal sprays, or eye drops. For a parenteral application, the drugs may be dissolved are suspended in a physiologically compatible diluent. Oily solutions, such as solutions in sesame oil, castor oil, and cotton seed oil, are also suitable as diluents. To increase the solubility, solution mediators, such as benzyl benzoate or benzyl alcohol, may be added.

In a special embodiment, the pharmaceutical or dermatological composition of the present invention contains further drugs and/or aids, preferably dexpanthenol. Dexpanthenol encourages the adhesion as an aid in aqueous compositions, such as aqueous sprays. Dexpanthenol is preferably used in nasal sprays, oral sprays, and eye drops/eye ointments. In a further embodiment, the pharmaceutical composition of the present invention additionally contains a pharmaceutically effective quantity of the protein filaggrin, either jointly with or spatially separated from the plant extract according to the invention.

Filaggrin is a histidine-rich cationic protein, and/or a group of isoform proteins, which originate in the keratinization process of the skin from profilaggrin. Filaggrin is a protein of the keratinizing epithelial cells of the epidermis, which aggregates the filaments and originates through post-translational modification of the profilaggrin in the keratinocytes. Filaggrin has structure-forming functions for the epidermis. A genetically-based lack of filaggrin has recently been formulated as one cause for the occurrence of a neurodermitis.

A further aspect of the present invention relates to the use of the plant extract or the pharmaceutical composition for the production of a pharmaceutical for the treatment of neurodermitis, allergies, inflammatory, itching dermatoses, mosquito bites, skin atrophy, allergic rhinitis, privinismus, otitis externa, bronchial asthma, Crohn's disease, ulcerative colitis, sarcoidosis, conjunctivitis, inflammatory-rheumatic diseases, and mycoses, or the prevention or treatment of phototoxic reactions. The plant extract or the pharmaceutical composition is preferably used in topical applications together with a pharmaceutically effective quantity of the protein filaggrin.

In another aspect, the present invention relates to the use of the plant extract according to the invention as a medication for the effective treatment of patients who respond inadequately or poorly to a therapy using a typical cortisone dose and/or reject cortisone treatment and/or may not be treated using cortisone-containing preparations because of side effects. In these cases, typically only the strongest therapeutic agents known up to this point (besides the cortisones)—calcineurin inhibitors—may be used instead, which very frequently only result in inadequate symptomatic relief of the symptoms, which are subjectively extraordinarily agonizing to the patients. Because the treatment can additionally be subject to severe side effects, the situation has still further problems. Therefore, we have searched for a possibility of supplementing and/or replacing calcineurin inhibitors by more effective and better compatible medications for the treatment of neurodermitis and also, vice versa, calcineurins. The present invention thus provides an effective therapy, which is free of side effects, of these patients (in the scope of the present invention designated as "therapy failures"). These therapy failures may, as specified above, be treated effectively using the *cannabis* extract according to the invention instead of cortisone, so that the calcineurin inhibitors do not have to be used instead, and vice versa.

The invention therefore also relates to a replacement therapy for cortisone and/or calcineurin-inhibitor therapy, the plant extract according to the invention being administered to the patient in a pharmaceutical or topical composition.

A further aspect of the present invention relates to the use of cannabinoids and/or the plant extracts according to the invention for the production of a pharmaceutical for the treatment of neurodermitis (atopical dermatitis), allergies, inflammatory, itching dermatoses, mosquito bites, skin atrophy, allergic rhinitis, privinismus, otitis externa, bronchial asthma, Crohn's disease, ulcerative colitis, sarcoidosis, conjunctivitis, mycoses, or inflammatory-rheumatic diseases, or the prevention or treatment of phototoxic reactions. These indications may also be treated jointly.

The cannabinoids are preferably used together with filaggrin in topical applications.

However, the treatment of neurodermitis and mycoses, optionally present jointly, using the plant extracts or cannabinoids according to the invention is particularly preferred.

In a further embodiment, the invention relates to the treatment of acute outbreaks of neurodermitis, which are possibly accompanied by strong itching. In these cases, a dosage of 0.1-5 g/l, in particular 0.5-1 g/l plant extract in a solvent, preferably isopropanol, has proven to be suitable for treating the acute outbreaks. Furthermore, a solid composition can be selected, which contains 2-70%, in particular 5 to 10% of the plant extract according to the invention.

The plant extracts according to the invention are therefore particularly suitable for the treatment of neurodermitis, because itching relief advantageously occurs. In a further preferred embodiment, the plant extract is to be applied in a lower dose (e.g., ⅓ or ½) for posttreatment.

The invention will be explained hereafter on the basis of examples, without being restricted to these examples, however.

1. Production of the Extract 1.1 Starting Material: The starting material is formed by flowers and/or flower-proximal leaves, preferably dried after harvest, of the low-THC industrial hemp variety (e.g., variety Futura 75). These are dried in dry air ("attic") and at low temperatures (<35° C.) hanging down on lines.

1.2 Preparation: During the preparation, the dried flowers and flower-proximal leaves are initially finely ground. The finely ground granules are subsequently introduced in a ratio of 1:4 to 1:5 (volume ratios) into various solvents and remain therein for 24 hours to 48 hours in light-proof brown bottles for the extraction procedure at room temperature, but not higher. The extract is subsequently filtered off and stored in light-proof bottles at approximately 2° C. Depending on the intended use, aqueous extracts using water or alcoholic extracts made of ethanol and isopropanol are suitable for the production of the extract. These are to be stored refrigerated until the development of suitable stabilizers—like the clinically highly effective creams which are producible therefrom (see below). An aqueous extract diluted in the ratio 1:5 is outstandingly suitable for nose, eye, and ear drops. Hair tinctures for the treatment of diseases of the scalp may be produced from the isopropyl extract. The ethanolic extract is thus suitable for the production of preparations (e.g., creams) for the remaining skin areas, beginning the treatment in the event of particularly pronounced symptoms, in particular itching, using an ethanolic or isopropanolic tincture also having proven itself here. Tinctures (undiluted) are also the agent of choice for the treatment of mycoses, i.e., for the first treatment stage, until the superficially visible efflorescences have died down, because they result in a particularly rapid initial effect.

2. Clinical Effectiveness 2.1 General

Additional topical or systemic pharmaceuticals, such as antihistamines, cortisone preparations, or calcineurin inhibitors, were not used as a supplement in a single one of the clinical applications described hereafter in the scope of medical treatment attempts.

All treated patients were made aware of the medical treatment attempt character of their individually titrated topical plant extract therapy and notified of the conventionally available therapeutic alternatives, with which they had typically previously been treated already with unsatisfactory results. All patients preferred the treatment using the plant extract of the present invention and/or a cream into which this plant extract was incorporated.

Undesired pharmaceutical effects, in particular allergic reactions, did not occur in any of the patients, who were partially treated up to 11 months and also intermittently upon lack of symptoms.

All patients requested information about how they could acquire low-THC *cannabis* preparations after the medical treatment attempt.

2.2 Treatment of Neurodermitis

In the scope of medical treatment attempts, 21 patients of various ages having chronic severe neurodermitis were treated an average of 7 to 10 days. All patients had in common:

Chronic severe course with unbearable itching, previous treatment using cortisones and calcineurin inhibitors with inadequate effect and/or termination of treatment provoked by side effects or refusal of the patients with respect to (further) cortisone therapy or treatment using calcineurin inhibitors.

In all patients, there was significant relief and/or abatement of the leading symptom of itching. The initial effect began within minutes after the first topical application. The duration of effect was approximately 12-24 hours. The most substantial efflorescences disappeared in 3-7 days. If the patients forgot to continue the local treatment because of the symptomatic relief and/or freeing, the disease symptoms recurred after days to weeks, but abated just as rapidly and significantly as under the initial therapy under renewed treatment. There was not a single therapy failure among the 21 patients treated using the extract.

2.3 Treatment of Mycoses

In the case of a very overweight 18-year-old patient, itching mycosis occurred in the area of the left sub-mammary fold, i.e., an intertriginous area. The application of a pharmaceutical composition according to the invention twice per day already resulted in significant symptom improvement, which could also be visually confirmed on the basis of the efflorescences, after 2 days. The symptoms were completely abated after a week of further treatment. A duration of at least 14 days is typically used for topical antimycotic therapy. A reoccurrence has not occurred in the following 5 summer months which have been able to be observed since then.

The conventional therapy duration of 14 days was applied in a 58-year-old male patient having a freshly occurring *Tinea pedis* having strong keratinization in the heel area, in order to also achieve effective antimycotic concentrations in lower lying skin areas. In addition to mechanical abrasion of the keratinized skin areas, the undiluted (applied in the ratio 1:4) fresh plant extract of the present invention was applied twice per day in the first three days of treatment for this patient. After the drying, this treatment was supplemented by the application of a cream, which contain this extract. From the 3rd to the 14th day of treatment, the cream was only still applied once or twice per day and wiped off after an action time of approximately one hour, in order to avoid laundry contamination because of the chlorophyll, which was not yet eliminated in the experimental batches. After this treatment, the mycosis was completely eliminated.

A 57-year-old female patient, who had suffered from genetically-related neurodermitis since her youth, reported for years of repeatedly recurring skin mycosis in the area of the neurodermitis-related damage of the integument, in particular in the intertriginous pedal interdigital area, which had previously been repeatedly affected. Since the patient has been treated using the topical preparations of the plant extract of the present invention, which has been 11 months in the meantime, not a single reoccurrence of a mycosis has occurred.

2.4 Treatment of Urticaria

In three patients, urticaria occurred on both forearms with pronounced rashes and extremely strong itching after garden work (pulling weeds in perennial beds). These symptoms were able to be abated completely and lastingly using immediately applied cream made of wool wax alcohol ointment (DAB 998), into which the alcoholic plant extract of the present invention was introduced until saturation, within 10-30 minutes (itching) and 30-60 minutes (rash) after a single application.

2.5 Treatment of Mosquito Bites

Mosquito bites having severe urticarial hives, approximately the size of a 5-mark piece, were able to be abated completely and lastingly in 4 cases in patients of various ages using a single application of a cream which contains the plant extract of the present invention.

In a further male 55-year-old patient, an extremely pronounced urticaria occurred in the area of the entire left middle and lower belly after an insect bite approximately 3 cm left of the paraumbilical. The finding was so severe that in this case, without clinical previous experience using the plant extract of the present invention, treatment would very probably have been local and systemic using dexamethasone (a particularly high-strength cortisone). After no sign of beginning anaphylactic shock was recognizable in the patient, however, firstly a treatment attempt using the plant extract of the present invention and/or a cream which contain this plant extract was performed under medical supervision. The itching was extensively abated already after approximately 20-30 minutes, the welt at the bite location had significantly receded, the swelling had regressed, and the rash was also relieved. Itching episodes did return over the next 5 days in this patient and the rash also had not yet completely disappeared, but these remaining symptoms reacted regularly to the renewed application of the cream.

3. Possible Action Mechanism

The rapid initial effect and the long action duration of the plant extract of the present invention indicate two different engagement points:

1. The rapid initial effect, which occurs within minutes, leads to the suspicion that the plant extract reacts, inter alia, with the itching receptors of the sensory nervous system of the skin. The fact that at this time the mediators of the mast cells (e.g., histamines and leukotrienes) have already been distributed and cause the agonizing symptoms in the skin tissue indicate this. An engagement point on the corresponding receptors may already be assumed because the symptomatic easing by scratching over the skin defect also destroys these receptors. Therefore, no action potentials which generate itching may still be fired. Therefore, the short-term active local effect of the plant extract is also to be explained via these receptors, although not by their destruction, but, for example, via a possible competitive effect.

2. The long effectiveness duration can be explained via an entirely different action mechanism, however. This is probably a secretion inhibition of the histamines and leukotrienes from the mast cells which is caused by a plant extract. The fact that two types of endocannabinoid receptors have already been detected on the mast cells of humans suggests this. It has thus also been shown that the control center of all cellularly-mediated immunological reactions, the mast cells, can also be decisively influenced by cannabinoids. It follows from this finding that the other diseases discussed in this invention, which are also mediated via mast cell reactions, are favorably influenced.

3. Furthermore, it follows from these considerations that all immune reactions mediated via mast cells are favorably influenced by cannabinoids.

The invention claimed is:

1. A composition consisting essentially of 0.1-5 grams/liter of an extract from at least one of the flowers, flower-proximal leaves, stalks, roots, and seeds of *Cannabis sativa* subspecies *sativa* variety Futura 75, isopropanol and sodium chloride, wherein the *Cannabis sativa* subspecies *sativa* variety Futura 75 has a THC content from 0.1 wt. % to 0.2 wt. %.

* * * * *